United States Patent
Gencheff

(10) Patent No.: US 10,646,693 B2
(45) Date of Patent: May 12, 2020

(54) METHOD OF CONTROLLING INTRAVASCULAR SHEATHS

(71) Applicant: Frontier Medical Devices, Inc., Marquette, MI (US)

(72) Inventor: Nelson E. Gencheff, Marquette, MI (US)

(*) Notice: Subject to any disclaimer, the term of this patent is extended or adjusted under 35 U.S.C. 154(b) by 1101 days.

(21) Appl. No.: 14/531,482

(22) Filed: Nov. 3, 2014

(65) Prior Publication Data

US 2015/0051483 A1   Feb. 19, 2015

Related U.S. Application Data

(63) Continuation-in-part of application No. 14/185,742, filed on Feb. 20, 2014, now abandoned.

(60) Provisional application No. 61/766,818, filed on Feb. 20, 2013.

(51) Int. Cl.

| | | |
|---|---|---|
| *A61M 25/01* | (2006.01) | |
| *A61B 17/00* | (2006.01) | |
| *A61M 25/00* | (2006.01) | |
| *A61M 25/06* | (2006.01) | |

(52) U.S. Cl.
CPC ... *A61M 25/0169* (2013.01); *A61B 2017/003* (2013.01); *A61M 2025/0004* (2013.01); *A61M 2025/0681* (2013.01)

(58) Field of Classification Search
CPC . A61M 25/0169; A61B 2017/003; A61B 5/05
USPC .................................................. 600/424
See application file for complete search history.

(56) References Cited

U.S. PATENT DOCUMENTS

| | | | | |
|---|---|---|---|---|
| 5,417,669 A | * | 5/1995 | Castaneda | A61M 25/0169 604/160 |
| 2005/0222558 A1 | * | 10/2005 | Baxter | A61B 18/1492 606/16 |
| 2007/0197939 A1 | * | 8/2007 | Wallace | A61B 5/6885 600/587 |
| 2012/0203064 A1 | * | 8/2012 | Wynberg | A61B 17/3421 600/106 |

* cited by examiner

*Primary Examiner* — Peter Luong
(74) *Attorney, Agent, or Firm* — Wood, Phillips, Katz, Clark & Mortimer

(57) ABSTRACT

A method of controlling intravascular sheaths including the steps of: a) obtaining a guide assembly having a body with a tubular wall bounding a passageway, the body having a length between axially spaced ends and an outer surface that tapers towards each of the spaced ends, the body flexible at each of the spaced ends to allow the spaced ends to bend transversely to the length of the body; b) directing the guide assembly into an operative state within a human body vessel; c) obtaining a first sheath having a tubular body extending around a passageway; and d) relatively moving the guide assembly body and first sheath to thereby direct the guide assembly body into the passageway on the first sheath and thereafter guidingly sliding the first sheath lengthwise against the outer surface of the guide assembly body to: a) advance the first sheath into the human body vessel; or b) withdraw the first sheath.

19 Claims, 5 Drawing Sheets

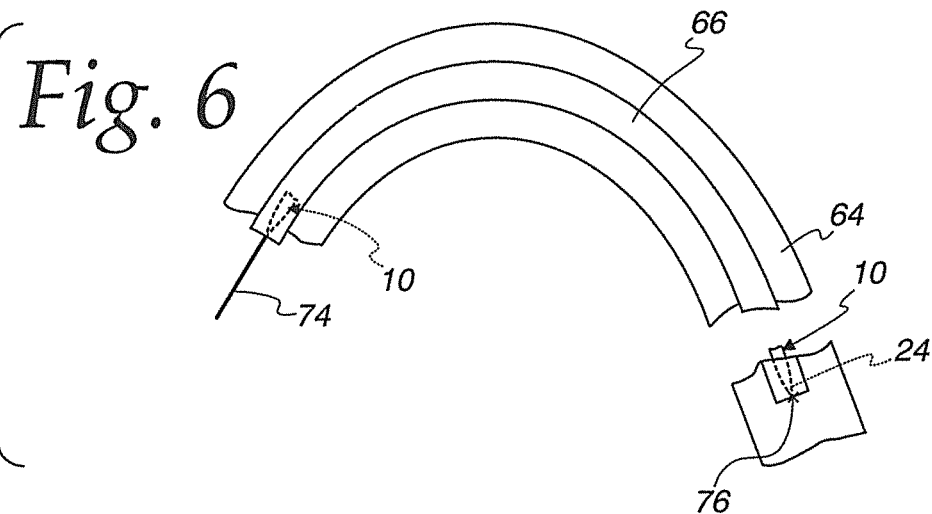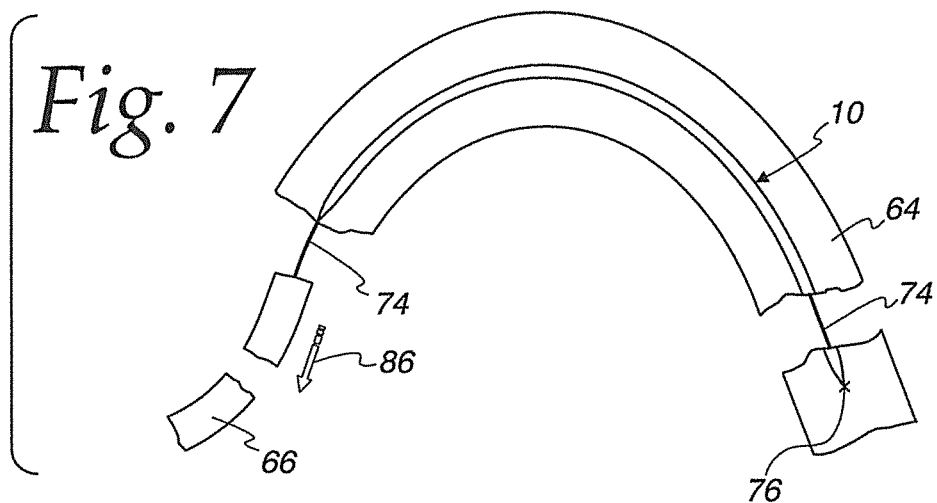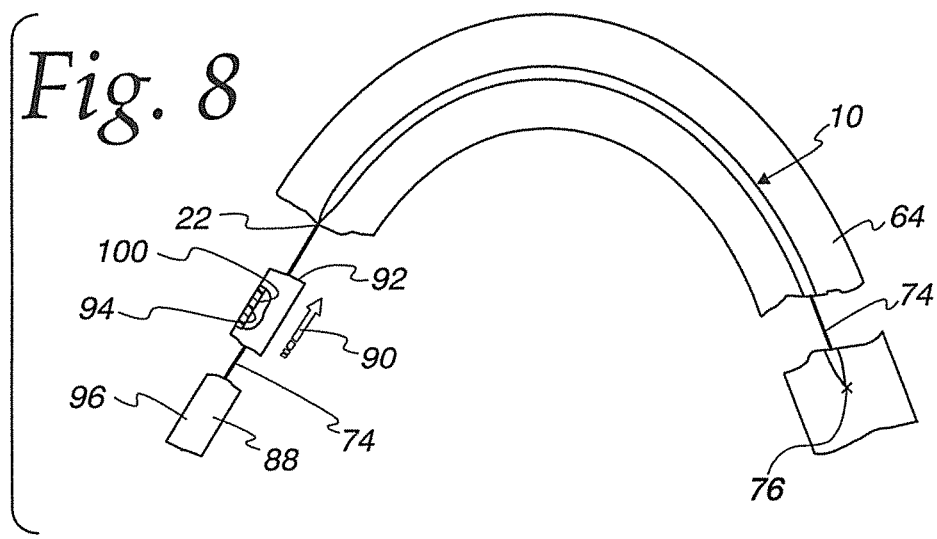

METHOD OF CONTROLLING INTRAVASCULAR SHEATHS

CROSS-REFERENCE TO RELATED APPLICATIONS

This application is a continuation-in-part of U.S. application Ser. No. 14/185,742 filed Feb. 20, 2014.

BACKGROUND OF THE INVENTION

Field of the Invention

This invention relates to sheaths as directed strategically into different human body vessels and, more particularly, to a method of controlling the introduction and withdrawal of such sheaths.

Background Art

Sheaths of different diameter and construction are commonly directed into different vessels on human bodies to assist the performance of different medical procedures. In certain portions of the human vessel network, sheaths are required to follow a circuitous route to their target location. This may make sheath manipulation difficult. For example, it may be difficult to effect sheath migration and exchanges across anatomically complex aortoiliac bifurcations. Current methods to achieve contralateral sheath positioning in acute angled and tortuous aortoiliac bifurcations are limited by poor sheath support which may lead to intravascular trauma. Failed contralateral sheath delivery may necessitate alternative vascular access strategies which may limit revascularization options.

Heretofore, the medical industry has contended with the above problems because no practical solution thereto has existed. At best, some of these complex procedures may be attempted by only highly skilled and experienced medical personnel. Even a highly skilled and experienced surgeon may find it difficult or impossible to effect sheath introduction and exchange in certain complex vascular geometry in a safe manner without undesirably long procedure times.

SUMMARY OF THE INVENTION

In one form, the invention is directed to a method of controlling intravascular sheaths. The method includes the step of obtaining a guide assembly having a body with a tubular wall bounding a passageway. The body has a central axis and a length between axially spaced ends. The body has an outer surface that tapers towards each of the spaced ends. The body is flexible at each of the spaced ends to allow the spaced ends to bend in a direction transversely to the length of the body. The method further includes the steps of: b) directing the guide assembly into an operative state within a human body vessel; c) obtaining a first sheath having a tubular body extending around a passageway and having a central axis; and d) relatively moving the guide assembly body and first sheath to thereby direct the guide assembly body into the passageway on the first sheath. Thereafter the first sheath slides guidingly lengthwise against the outer surface of the guide assembly body to thereby one of: a) advance the first sheath into the human body vessel; and b) withdraw the first sheath from the human body vessel.

In one form, the method further includes the steps of obtaining a guide wire, directing the guide wire into the human body vessel, and with the guide wire in the guide assembly passageway sliding the guide assembly body guidingly against the guide wire to thereby place the guide assembly in the operative state.

In one form, step d) is carried out to withdraw the first sheath from the human body vessel while leaving the guide assembly in its operative state. The method further includes the steps of obtaining a second sheath having a tubular body extending around a passageway and having a central axis and directing one of the guide assembly body ends into the passageway on the second sheath and thereafter guidingly sliding the second sheath lengthwise against the outer surface of the guide assembly body to thereby advance the second sheath into the human body vessel.

In one form, the method further includes the step of moving the guide assembly from a state fully separated from the first sheath within the human body vessel relative to the first sheath by directing one of the spaced ends of the guide assembly body into the passageway on the first sheath and thereafter sliding the outer surface lengthwise against and relative to the first sheath to cause the guide assembly to be moved into its operative state.

In one form, the guide assembly body has a "U" shape with the guide assembly in its operative state in the human body vessel.

In one form, the step of obtaining a guide assembly involves obtaining a guide assembly wherein the guide assembly has a marker thereon. The method further includes the step of tracking location of the guide assembly through use of a detector that is capable of sensing where the marker is located.

In one form, the marker is a radio opaque marker.

In one form, the first and second sheaths have different diameters.

In one form, the step of obtaining a guide assembly involves obtaining a guide assembly with a body having a length between 85 and 115 cm.

In one form, the method further includes the step of applying a lubricant to the guide assembly body.

In one form, the step of applying a lubricant involves applying a lubricant to the outer surface of the tubular wall and to a surface on the tubular wall bounding the passageway on the guide assembly.

In one form, the body has a length between where the outer surface tapers towards each of the spaced ends of the body that is made from a material that is more rigid than a material defining the outer surface where the outer surface tapers towards the spaced ends.

In one form, step d) is carried out to withdraw the first sheath from the human body vessel while leaving the guide wire in the human body vessel.

In one form, the invention is directed to the guide assembly as described above.

In one form, the guide assembly is in an operative state within a human body vessel.

In one form, the guide assembly is provided in combination with a sheath. The sheath is a tubular body extending around a passageway wherein the body of the guide assembly resides within the sheath passageway.

In one form, the guide assembly is provided in combination with a guide wire. The guide wire extends through the passageway in the guide assembly body.

In one form, there is a marker either on the outer surface of the guide assembly body or embedded in the guide assembly body. The marker is configured to be sensed by a detector to facilitate tracking of movement of the marker and thereby movement of the guide assembly body within a human body vessel.

In one form, the marker is a radio opaque marker.

In one form, the guide assembly body has a length between 85 and 115 cm.

BRIEF DESCRIPTION OF THE DRAWINGS

FIGS. 5-10 show a sequence of steps carried out to remove one sheath in a human body vessel situated to access a target location and replace that sheath with another sheath to access the same target location.

DETAILED DESCRIPTION OF THE PREFERRED EMBODIMENT

Figure 1:
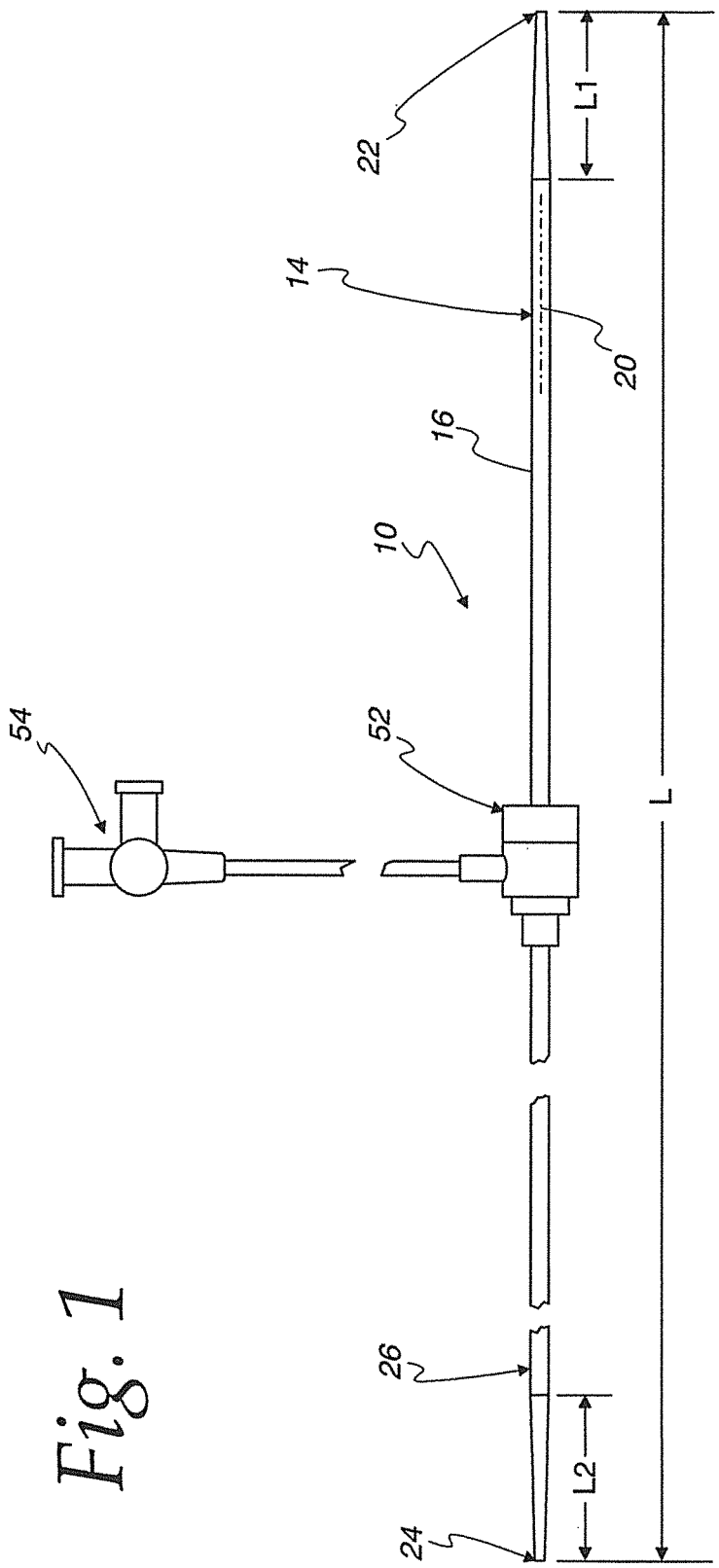
FIG. 1 is a side elevation view of one form of guide assembly, according to the present invention, usable to control introduction and exchange of intravascular sheaths.
Figure 2:
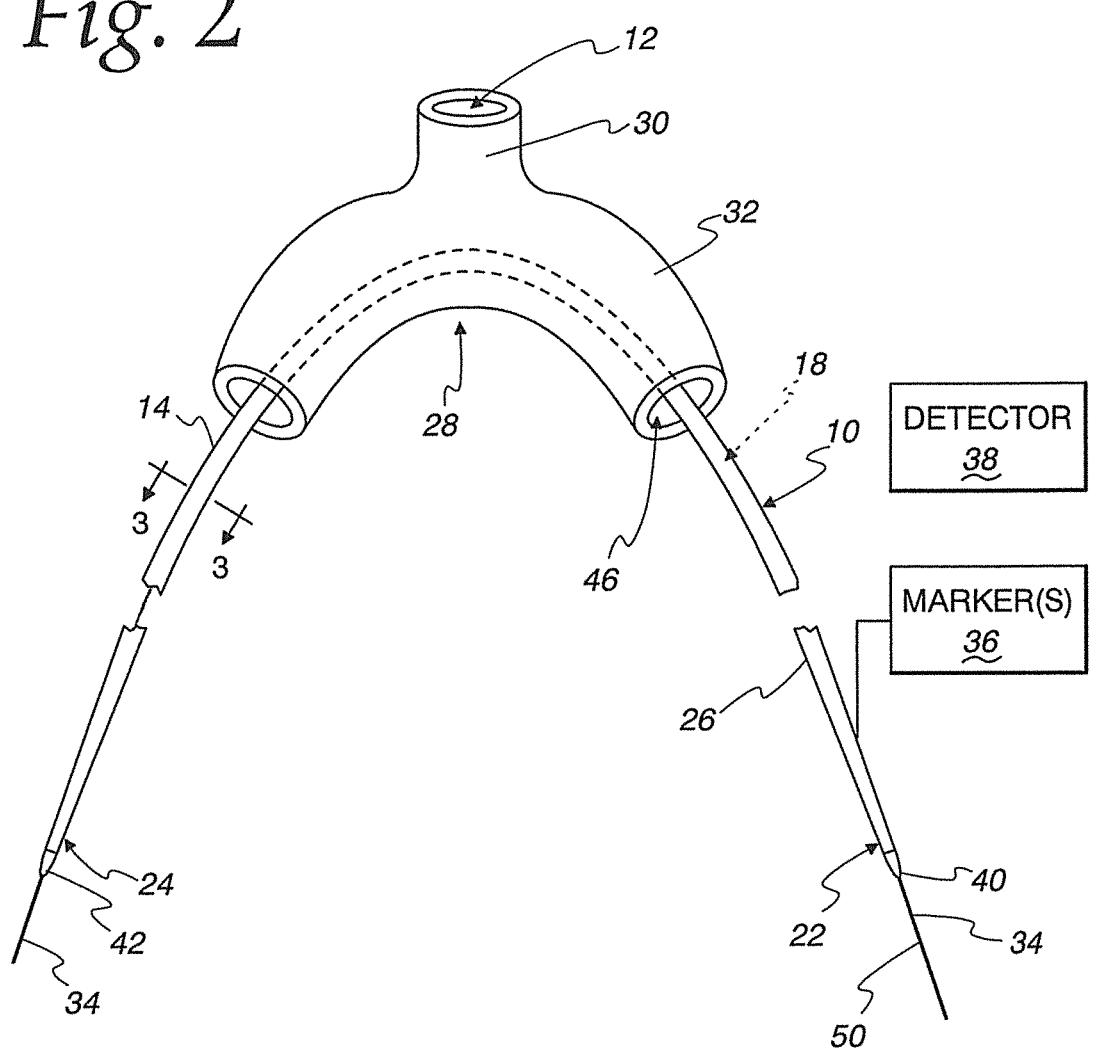
FIG. 2 is a fragmentary view of a portion of a vessel network in a human body with the guide assembly of FIG. 1 in an operative state.
Figure 3:
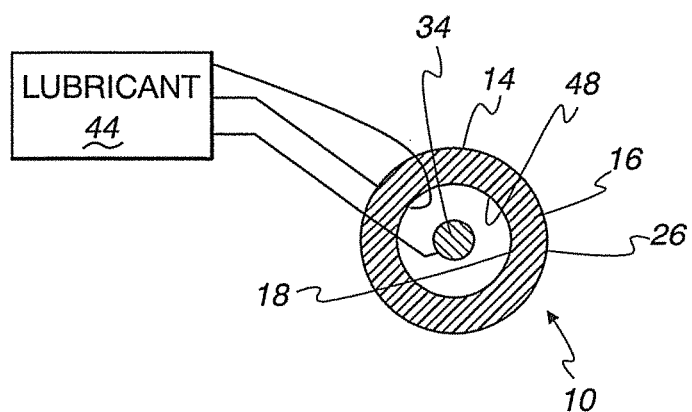
FIG. 3 is an enlarged, cross-sectional view of the guide assembly taken along line 3-3 of FIG. 2.

In FIGS. 1-3, a guide assembly, according to the present invention, is shown at 10, that is usable to control intravascular delivery of sheaths and exchange of sheaths during medical procedures performed through a human vessel network 12. The guide assembly 10 has a body 14 with a tubular wall 16 bounding a passageway 18. The body 14 has a central axis 20 and a length L between axially spaced ends 22, 24. The body 14 has an outer surface 26 that tapers continuously towards each of the spaced ends 22, 24.

The entire body 14 is preferably made from a flexible material, with the tapered lengths L1, L2 at the ends 22, 24 preferably being more flexible than part, or all, of the remainder of the body 14. This greater flexibility may result from the reduced cross-sectional area and additionally by reason of the tapered lengths L1, L2 being made from a more flexible material. The flexibility of the tapered lengths L1, L2 allows the ends 22, 24 to bend in a direction transversely to the length of the body 14, while at the same time maintaining sufficient flexibility that they are not prone to bunching or kinking with the guide assembly 10 utilized as described hereinbelow.

While the guide assembly 10 can be utilized at virtually any desired location in the human vessel network 12, it is shown at an exemplary application at the juncture at 28 between the aorta 30 and iliac artery 32. In this operative state, the body 14 has an inverted "U" shape.

Preferably, the guide assembly 10 is directed into its operative state utilizing a guide wire 34. The passageway 18, particularly at the tapered ends, is configured to accommodate a conventional 0.038 inch guide wire. Typically, the guide wire 34 would be directed into the vessel(s) in a preselected path. With the guide wire 34 in the passageway 18, the guide assembly 10 is slid against the guide wire 34 until the operative state is realized.

The guide assembly 10 may have one or more markers 36 strategically placed thereon, such as at the proximal end or distal ends. The markers 36 may be placed on the surface 26 or embedded in the body 14. Through a detector 38, movement of the markers 36 can be sensed to thereby determine the position of the guide assembly 10. The body 14 may be made radio opaque for this purpose. This allows the surgeon to visualize the subject's intravascular geometry as the guide assembly 10 is moved in the vessel network 12.

To avoid any internal trauma, the free ends 40, 42 of the body 14 may be made from a soft material. The free ends 40, 42 are rounded to avoid hangup and vascular trauma.

By reason of the described construction for the tapered lengths L1, L2, atraumatic entry into the vessel network 12, and also entry and exit into and out of an existing sheath, without losing vascular position, can be effected.

A lubricant 44 is strategically applied to facilitate relative movement between the guide wire 34, body 14, and inside 46 of the vessel network 12. For example, a lubricious material may be used to coat the inside surface 48 of the body 14 bounding the passageway 18, the outer surface 26, and an outer surface 50 of the guide wire 34. This may reduce intravascular and wire frictional forces during deployment of the guide assembly 10.

For typical procedures, the overall length L of the guide assembly 10 is on the order of 100 cm±15 cm. This is not a requirement, however.

The body 14 will typically be made available in sizes ranging from 5 Fr to 8 Fr. The body 14 may be formed by extrusion or otherwise by methods known to those skilled in the art.

The body 14 may incorporate a monitoring port 52 with a suitable access valve at 54 engineered based upon the particular procedure to be performed.

Figure 4:
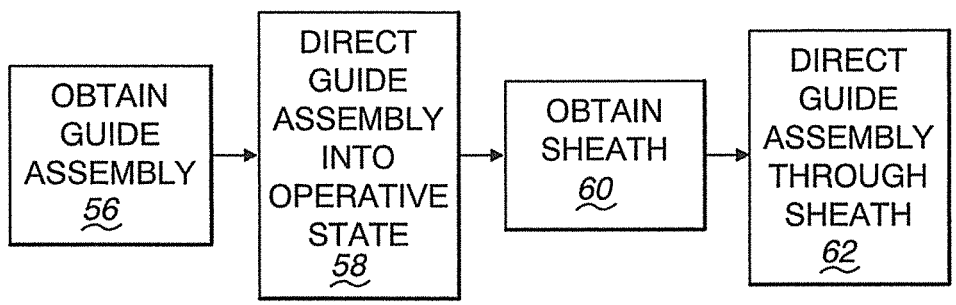
FIG. 4 is a flow diagram representation of a method of controlling intravascular sheaths using the inventive guide assembly.

With the above-described guide assembly 10, a method of controlling intravascular sheaths can be carried out in its most general form as shown in flow diagram form in FIG. 4.

As shown at block 56, the guide assembly as described above is obtained.

As shown at block 58, the guide assembly is directed into an operative state within a human body vessel.

As shown at block 60, a first sheath is obtained having a tubular body extending around a passageway and having a central axis.

As shown at block 62, the guide assembly body and first sheath are relatively moved to direct the guide assembly into the passageway on the first sheath. Thereafter, the first sheath is slid guidingly lengthwise against the outer surface of the guide assembly body to thereby one of: a) advance the first sheath into a human body vessel; and b) withdraw the first sheath from a human body vessel.

One more specific method of controlling intravascular sheaths, utilizing the inventive guide assembly 10, is shown in FIGS. 5-10. In each of these Figures, the guide assembly 10 is shown in a U-shaped configuration conforming to the configuration of a generic body vessel 64.

Figure 5:
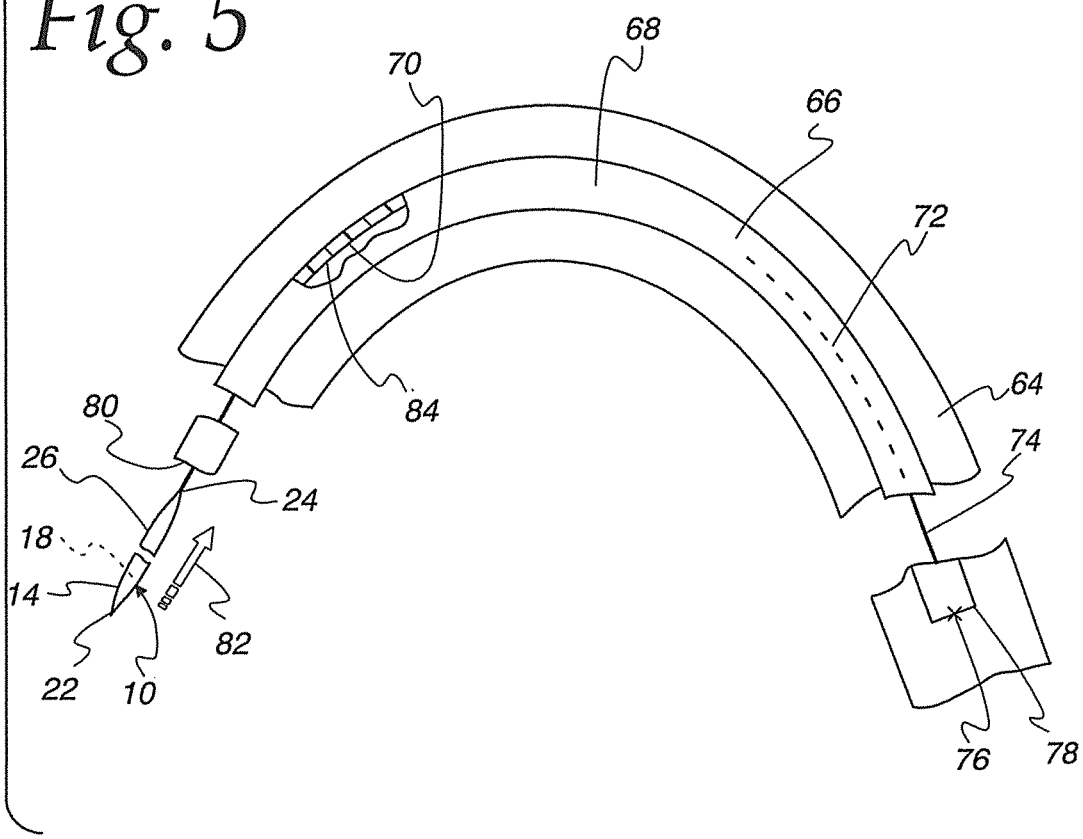

In FIG. 5, the first sheath 66 is shown directed into the vessel 64. The sheath 66 has a tubular body 68 extending around a passageway 70. The tubular body 68 has a central axis 72 extending along the length of the body 68.

The sheath 66 is placed in the FIG. 5 position through the conventional use of a guide wire 74 that is controllably directed to an intravascular target location 76. By sliding the tubular body 68 along the guide wire 74, the distal end 78 of the tubular body 68 can be placed at the target location 76.

When it is desired to withdraw the sheath 66 using the guide assembly 10, the distal end 24 of the guide assembly body 14 is introduced to the passageway 70 through the proximal end 80 of the tubular body 68. With the guide assembly 10 initially in the fully separated state of FIG. 5, and the guide wire 74 extending into the passageway 18, the guide assembly 10 can be advanced in the direction of the arrow 82 through the passageway 70 on the first sheath 66 until the end 24 resides at or adjacent to the target location 76, as shown in FIG. 6. As the tubular body 68 is advanced, the guide wire 74 moves guidingly within the passageway 18, with the outer surface 26 of the body 14 sliding guidingly against an inside surface 84 that bounds the tubular body passageway 70.

With the guide assembly 10 in its operative state of FIG. 6, the first sheath 66 can be withdrawn by being slid guidingly against and relative to the guide assembly 10 in the direction of the arrow 86, as seen in FIG. 7. As this occurs, the guide assembly 10 remains in its operative state so that the position of the guide wire 74 is maintained. The first sheath 66 can then be fully withdrawn from the vessel 64 and separated from the guide wire 74.

Figure 9:
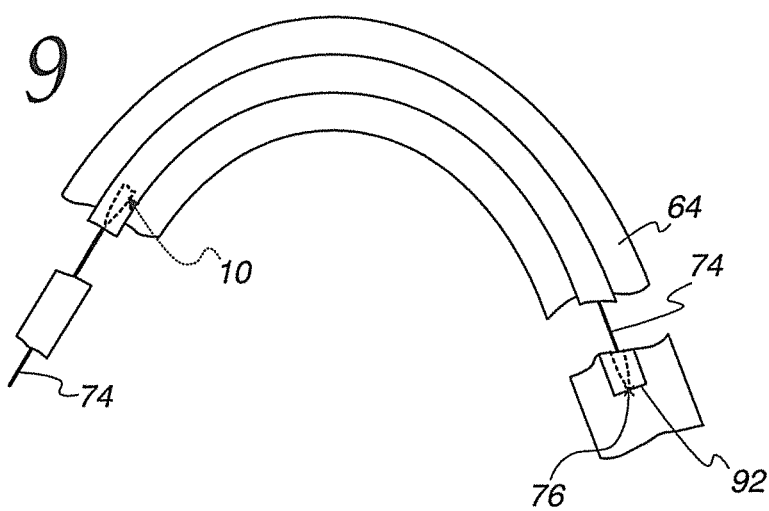

As shown in FIG. 8, a second sheath 88 can then be advanced over the guide assembly 10 in its operative state, in the direction of the arrow 90 until it resides within the vessel 64 and a distal end 92 thereof is at the target location 76, as seen in FIG. 9. The tapered configuration of the body end 22 facilitates guided entry into a passageway 94 defined by a tubular body 96 at the distal end 92 thereof.

Figure 10:
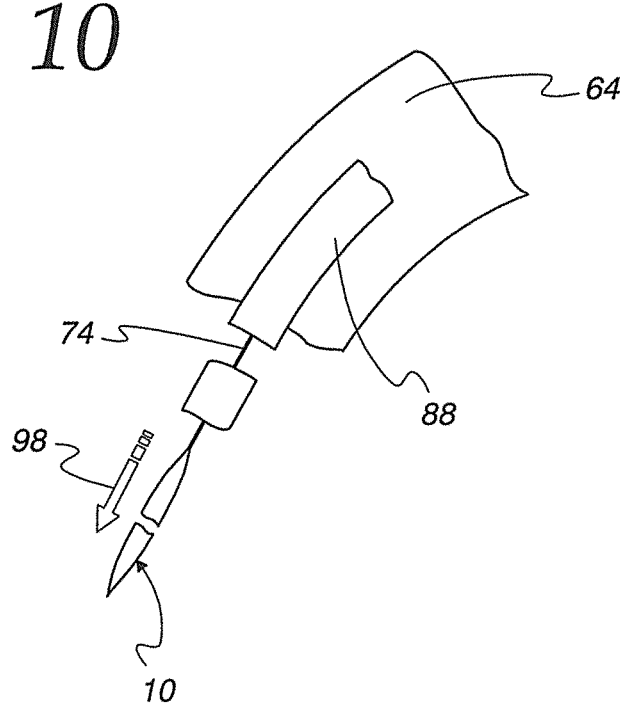

As seen in FIG. 10, the guide assembly 10 can then be withdrawn from the second sheath 88 and the vessel 64 by sliding the guide assembly in the direction of the arrow 98 guidingly against the guide wire 74 and a surface 100 bounding the passageway 94.

The second sheath 88 may have the same configuration as the first sheath or have a different configuration due to a different construction, diameter, etc.

With a single guide assembly configuration, multiple sheath diameters and lengths can be accommodated. A stable platform is provided for sheath introduction and exchange in the event of new equipment requirements during a peripheral vascular intervention. While the guide assembly 10 is usable for contralateral vascular access, it may have applications to other vascular territories and procedures during which sheath introduction and exchange become necessary and where maintenance of wire position is important.

The foregoing disclosure of specific embodiments is intended to be illustrative of the broad concepts comprehended by the invention.

The invention claimed is:

1. A method of controlling intravascular sheaths, the method comprising the steps of:
   a) obtaining a guide assembly comprising a body with a tubular wall bounding a passageway, the body having a central axis and a length between axially spaced ends, the body having an outer surface that tapers towards each of the spaced ends, the body flexible at each of the spaced ends to allow the spaced ends to bend in a direction transversely to the length of the body;
   b) directing the guide assembly into an operative state within a human body vessel;
   c) obtaining a first sheath having a tubular body extending around a passageway and having a central axis;
   d) relatively moving the guide assembly body and first sheath to thereby direct the guide assembly body into the passageway on the first sheath; and
   e) with the guide assembly body directed into the passageway on the first sheath and the guide assembly in the operative state within the human body vessel, guidingly sliding the first sheath lengthwise against the outer surface of the guide assembly body to thereby one of: a) advance the first sheath into the human body vessel; and b) withdraw the first sheath from the human body vessel.

2. The method of controlling intravascular sheaths according to claim 1 further comprising the steps of obtaining a guide wire, directing the guide wire into the human body vessel, and with the guide wire in the guide assembly passageway sliding the guide assembly body guidingly against the guide wire to thereby place the guide assembly in the operative state.

3. The method of controlling intravascular sheaths according to claim 2 wherein step d) is carried out to withdraw the first sheath from the human body vessel while leaving the guide wire in the human body vessel.

4. The method of controlling intravascular sheaths according to claim 2 wherein step e) is carried out to withdraw the first sheath from the human body vessel while leaving the guide assembly in its operative state and further comprising the steps of obtaining a second sheath having a tubular body extending around a passageway and having a central axis and directing one of the guide assembly body ends into the passageway on the second sheath and thereafter guidingly sliding the second sheath lengthwise against the outer surface of the guide assembly body that is left in the operative state to thereby advance the second sheath into the human body vessel.

5. The method of controlling intravascular sheaths according to claim 4 wherein the first and second sheaths have different diameters.

6. The method of controlling intravascular sheaths according to claim 1 further comprising the step of moving the guide assembly from a state fully separated from the first sheath within the human body vessel relative to the first sheath by directing one of the spaced ends of the guide assembly body into the passageway on the first sheath and thereafter sliding the outer surface lengthwise against and relative to the first sheath to cause the guide assembly to be moved into its operative state.

7. The method of controlling intravascular sheaths according to claim 1 wherein the guide assembly body has a "U" shape with the guide assembly in its operative state in the human body vessel.

8. The method of controlling intravascular sheaths according to claim 1 wherein the step of obtaining a guide assembly comprises obtaining a guide assembly wherein the guide assembly has a marker thereon and further comprising the step of tracking location of the guide assembly through use of a detector that is capable of sensing where the marker is located.

9. The method of controlling intravascular sheaths according to claim 8 wherein the marker is a radio opaque marker.

10. The method of controlling intravascular sheaths according to claim 1 wherein the step of obtaining a guide assembly comprises obtaining a guide assembly with a body having a length between 85 and 115 cm.

11. The method of controlling intravascular sheaths according to claim 1 further comprising the step of applying a lubricant to the guide assembly body.

12. The method of controlling intravascular sheaths according to claim 11 wherein the step of applying a lubricant comprises applying a lubricant to the outer surface of the tubular wall and to a surface on the tubular wall bounding the passageway on the guide assembly.

13. The method of controlling intravascular sheaths according to claim 1 wherein the body has a length between where the outer surface tapers towards each of the spaced ends of the body that is made from a material that is more rigid than a material defining the outer surface where the outer surface tapers towards the spaced ends.

14. The method of controlling intravascular sheaths according to claim 1 wherein the guide assembly body has a length between 85 and 115 cm.

15. The method of controlling intravascular sheaths according to claim 1 wherein the step of obtaining a guide assembly comprises obtaining a guide assembly wherein the outer surface of the body tapers continuously towards each of the spaced ends.

16. A method of controlling intravascular sheaths, the method comprising the steps of:
   a) obtaining a guide assembly comprising a body with a tubular wall bounding a passageway, the body having an outer surface, a central axis and a length between axially spaced ends, the body having an outer surface that tapers towards each of the spaced ends, the body flexible at each of the spaced ends to allow the spaced ends to bend in a direction transversely to the length of the body;
   b) directing the guide assembly into an operative state within a human body vessel with the guide assembly body in a first position wherein one of the axially spaced ends of the guide assembly body is adjacent to a target location;
   c) obtaining a first sheath having a tubular body extending around a passageway and having a central axis; and
   d) one of either: i) starting with the guide assembly body within the passage on the first sheath, guidingly sliding the first sheath lengthwise against the outer surface of the guide assembly body while maintaining the guide assembly body in the first position to thereby withdraw the first sheath from the human body vessel; and ii) starting with the first sheath separated from the guide assembly body and the guide assembly body maintained in the first position, moving the guide assembly body and first sheath relative to each other so that the guide assembly body is within the passageway in the first sheath and thereafter guidingly sliding the first sheath lengthwise against the outer surface of the guide assembly body to thereby situate an end of the first sheath adjacent to the target location.

17. The method of controlling intravascular sheaths according to claim 16 wherein with the guide assembly in the operative state with the guide assembly body in the first position, both of the axially spaced ends of the guide assembly body reside within the human body vessel.

18. A method of controlling intravascular sheaths, the method comprising the steps of:
   a) obtaining a guide assembly comprising a body with a tubular wall bounding a passageway, the body having an outer surface, a central axis and a length between axially spaced ends, the body having an outer surface that tapers towards each of the spaced ends, the body flexible at each of the spaced ends to allow the spaced ends to bend in a direction transversely to the length of the body;
   b) directing the guide assembly into an operative state within a human body vessel with the guide assembly body in a first position wherein one of the axially spaced ends of the guide assembly body is adjacent to a target location;
   c) obtaining a first sheath having a tubular body extending around a passageway and having a central axis; and
   d) one of either: i) starting with the guide assembly body within the passage on the first sheath, guidingly sliding the first sheath lengthwise against the outer surface of the guide assembly body while maintaining the guide assembly body in the first position to thereby withdraw the first sheath from the human body vessel; and ii) starting with the first sheath separated from the guide assembly body and the guide assembly body maintained in the first position, moving the guide assembly body and first sheath relative to teach other so that the guide assembly body is within the passageway in the first sheath and thereafter guidingly sliding the first sheath lengthwise against the outer surface of the guide assembly body to thereby situate an end of the first sheath adjacent to the target, wherein with the guide assembly in the operative state with the guide assembly body in the first position, both of the axially spaced ends of the guide assembly body reside within the human body vessel.

19. A method of controlling intravascular sheaths, the method comprising the steps of:
   a) obtaining a guide assembly comprising a body with a tubular wall bounding a passageway, the body having an outer surface, a central axis and a length between axially spaced ends, the body having an outer surface that tapers towards each of the spaced ends, the body flexible at each of the spaced ends to allow the spaced ends to bend in a direction transversely to the length of the body;
   b) directing the guide assembly into an operative state within a human body vessel with the guide assembly body in a first position wherein one of the axially spaced ends of the guide assembly body is adjacent to a target location;
   c) obtaining a first sheath having a tubular body extending around a passageway and having a central axis; and
   d) one of either: i) starting with the guide assembly body within the passage on the first sheath, guidingly sliding the first sheath lengthwise against the outer surface of the guide assembly body while maintaining the guide assembly body in the first position to thereby withdraw the first sheath from the human body vessel; and ii) starting with the first sheath separated from the guide assembly body and the guide assembly body maintained in the first position, moving the guide assembly body and first sheath relative to teach other so that the guide assembly body is within the passageway in the first sheath and thereafter guidingly sliding the first sheath lengthwise against the outer surface of the guide assembly body to thereby situate an end of the first sheath adjacent to the target, wherein with the guide assembly in the operative state with the guide assembly body in the first position, the guide assembly body is in a "U" shape at a junction between an aorta and iliac artery.

* * * * *

UNITED STATES PATENT AND TRADEMARK OFFICE
CERTIFICATE OF CORRECTION

PATENT NO. : 10,646,693 B2
APPLICATION NO. : 14/531482
DATED : May 12, 2020
INVENTOR(S) : Nelson E. Gencheff Page 1 of 2

It is certified that error appears in the above-identified patent and that said Letters Patent is hereby corrected as shown below:

On the Title Page

Under abstract "19 Claims, 5 Drawing Sheets" should read --21 Claims, 5 Drawing Sheets--.

In the Claims

Column 7, Line 43-Column 8, Line 57, (approx.), should read:
--18. The method of controlling intravascular sheaths according to claim 16 wherein the guide assembly in the operative state with the guide assembly body in the first position, the guide assembly body is in a "U" shape at a junction between an aorta and iliac artery.

19. The method of controlling intravascular sheaths according to claim 16 further comprising the steps of obtaining a guide wire, directing the guide wire into the human body vessel, and with the guide wire in the guide assembly passageway sliding the guide assembly body guidingly against the guide wire to thereby place the guide assembly in the operative state.

20. A method of controlling intravascular sheaths, the method comprising the steps of:
a) obtaining a guide assembly comprising a body with a tubular wall bounding a passageway, the body having an outer surface, a central axis and a length between axially spaced ends, the body flexible at each of the spaced ends to allow the spaced ends to bend in a direction transversely to the length of the body;
b) directing the guide assembly into an operative state within a human body vessel with the guide assembly body in a first position wherein one of the axially spaced ends of the guide assembly body is adjacent to a target location and the other of the axially spaced ends of the guide assembly resides within the human body;
c) obtaining a first sheath having a tubular body extending around a passageway and having a central axis; and
d) one of either: i) starting with the guide assembly body within the passage on the first sheath, guidingly sliding the first sheath lengthwise against the outer surface of the guide assembly Signed and Sealed this
Sixteenth Day of March, 2021

Drew Hirshfeld
*Performing the Functions and Duties of the
Under Secretary of Commerce for Intellectual Property and
Director of the United States Patent and Trademark Office* body while maintaining the guide assembly body in the first position to thereby withdraw the first sheath from the human body vessel; and ii) starting with the first sheath separated from the guide assembly body and the guide assembly body maintained in the first position, moving the guide assembly body and first sheath relative to each other so that the guide assembly body is within the passageway in the first sheath and thereafter guidingly sliding the first sheath lengthwise against the outer surface of the guide assembly body to thereby situate an end of the first sheath adjacent to the target location.

21. A method of controlling intravascular sheaths, the method comprising the steps of:
a) obtaining a guide assembly comprising a body with a tubular wall bounding a passageway, the body having an outer surface, a central axis and a length between axially spaced ends, the body flexible at each of the spaced ends to allow the spaced ends to bend in a direction transversely to the length of the body;
b) directing the guide assembly into an operative state within a human body vessel with the guide assembly body in a first position wherein one of the axially spaced ends of the guide assembly body is adjacent to a target location and the guide assembly is in a "U" shape at a junction between an aorta and iliac artery;
c) obtaining a first sheath having a tubular body extending around a passageway and having a central axis; and
d) one of either: i) starting with the guide assembly body within the passage on the first sheath, guidingly sliding the first sheath lengthwise against the outer surface of the guide assembly body while maintaining the guide assembly body in the first position to thereby withdraw the first sheath from the human body vessel; and ii) starting with the first sheath separated from the guide assembly body and the guide assembly body maintained in the first position, moving the guide assembly body and first sheath relative to each other so that the guide assembly body is within the passageway in the first sheath and thereafter guidingly sliding the first sheath lengthwise against the outer surface of the guide assembly body to thereby situate an end of the first sheath adjacent to the target location.--.